US008980924B2

(12) United States Patent
Petrukhin et al.

(10) Patent No.: US 8,980,924 B2
(45) Date of Patent: Mar. 17, 2015

(54) NON-RETINOID RBP4 ANTAGONIST FOR TREATMENT OF AGE-RELATED MACULAR DEGENERATION AND STARGARDT DISEASE

(75) Inventors: Konstantin Petrukhin, New Windsor, NY (US); Janet Sparrow, New York, NY (US); Rando Allikmets, Cornwall on Hudson, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 13/988,754

(22) PCT Filed: Nov. 22, 2011

(86) PCT No.: PCT/US2011/061763
§ 371 (c)(1),
(2), (4) Date: Oct. 10, 2013

(87) PCT Pub. No.: WO2012/071369
PCT Pub. Date: May 31, 2012

(65) Prior Publication Data
US 2014/0031392 A1 Jan. 30, 2014

Related U.S. Application Data

(60) Provisional application No. 61/416,961, filed on Nov. 24, 2010.

(51) Int. Cl.
*A61K 31/451* (2006.01)
(52) U.S. Cl.
CPC .................................. *A61K 31/451* (2013.01)
USPC ....................................................... 514/330
(58) Field of Classification Search
USPC ....................................................... 514/330
See application file for complete search history.

(56) References Cited

U.S. PATENT DOCUMENTS

| | | | |
|---|---|---|---|
| 4,797,419 A | 1/1989 | Moos et al. | |
| 4,895,841 A | 1/1990 | Sugimoto et al. | |
| 5,231,083 A | 7/1993 | Linz et al. | |
| 5,312,814 A | 5/1994 | Biller et al. | |
| 5,523,430 A | 6/1996 | Patel et al. | |
| 5,532,243 A | 7/1996 | Gilligan et al. | |
| 5,703,091 A | 12/1997 | Steiner et al. | |
| 5,716,974 A | 2/1998 | Camaggi et al. | |
| 5,891,889 A | 4/1999 | Anthony et al. | |
| 5,958,942 A | 9/1999 | Takatani et al. | |
| 6,372,793 B1 | 4/2002 | Lamango et al. | |
| 6,638,980 B1 | 10/2003 | Su et al. | |
| 8,168,783 B2 | 5/2012 | Kokubo et al. | |
| 2003/0195195 A1 | 10/2003 | Haviv et al. | |
| 2004/0097575 A1 | 5/2004 | Doherty et al. | |
| 2004/0167185 A1 | 8/2004 | Shankar et al. | |
| 2004/0180877 A1 | 9/2004 | Peters et al. | |
| 2004/0220171 A1 | 11/2004 | Pauls et al. | |
| 2006/0074121 A1 | 4/2006 | Chen et al. | |
| 2006/0089378 A1 | 4/2006 | Xia et al. | |
| 2006/0135460 A1 | 6/2006 | Widder et al. | |
| 2006/0172992 A1 | 8/2006 | Yokoyama et al. | |
| 2006/0270688 A1 | 11/2006 | Chong et al. | |
| 2007/0015827 A1 | 1/2007 | Widder et al. | |
| 2007/0254911 A1 | 11/2007 | Xia et al. | |
| 2008/0051409 A1 | 2/2008 | Gmeiner et al. | |
| 2008/0139552 A1 | 6/2008 | Bissantzet et al. | |
| 2008/0254140 A1 | 10/2008 | Widder et al. | |
| 2009/0054532 A1 | 2/2009 | Mata et al. | |
| 2009/0082362 A1 | 3/2009 | Bakthavatchalam et al. | |
| 2009/0088435 A1* | 4/2009 | Mata et al. | 514/239.5 |
| 2009/0143376 A1 | 6/2009 | Milburn et al. | |
| 2010/0022530 A1 | 1/2010 | Schiemann et al. | |
| 2010/0063047 A1 | 3/2010 | Borchardt et al. | |
| 2010/0168080 A1 | 7/2010 | Khamrai et al. | |

(Continued)

FOREIGN PATENT DOCUMENTS

| | | |
|---|---|---|
| DE | 4130514 A1 | 3/1993 |
| EP | 1190710 | 3/2002 |

(Continued)

OTHER PUBLICATIONS

International Search Report in connection with PCT/US2014/026813 issued Jul. 18, 2014.
Written Opinion of the International Searching Authority issued Jul. 18, 2014 in connection with PCT/US2014/026813.
Notification of Transmittal of the International Search Report and the Written Opinion of the International Searching Authority, or the Declaration issued Jul. 18, 2014 in connection with PCT/US2014/026813.
International Search Report in connection with PCT/US2014/026523 issued Aug. 22, 2014.
Written Opinion issued Aug. 22, 2014 in connection with PCT/US2014/026523.

(Continued)

*Primary Examiner* — Rei-tsang Shiao
(74) *Attorney, Agent, or Firm* — John P. White; Cooper & Dunham LLP

(57) ABSTRACT

A method for treating bisretinoid-mediated macular degeneration in a mammal afflicted therewith comprising administering to the mammal an effective amount of a compound having the structure:

or an ester or a pharmaceutically acceptable salt thereof.

14 Claims, 12 Drawing Sheets

(56) References Cited

U.S. PATENT DOCUMENTS

| | | |
|---|---|---|
| 2010/0292206 A1 | 11/2010 | Kasai et al. |
| 2011/0003820 A1 | 1/2011 | Henrich et al. |
| 2011/0118236 A1 | 5/2011 | Mochizuki et al. |
| 2011/0201657 A1 | 8/2011 | Boueres et al. |
| 2011/0251182 A1 | 10/2011 | Sun et al. |
| 2011/0251187 A1 | 10/2011 | Kasai et al. |
| 2011/0257196 A1 | 10/2011 | Lu et al. |
| 2011/0294854 A1 | 12/2011 | Searle et al. |
| 2011/0319393 A1 | 12/2011 | Chassaing et al. |
| 2011/0319412 A1 | 12/2011 | Sakagami et al. |
| 2012/0010186 A1 | 1/2012 | Lachance et al. |
| 2012/0065189 A1 | 3/2012 | Takahashi et al. |
| 2012/0071489 A1 | 3/2012 | Kasai et al. |
| 2012/0071503 A1 | 3/2012 | Cosford et al. |
| 2012/0077844 A1 | 3/2012 | Cavezza et al. |
| 2012/0077854 A1 | 3/2012 | Petrassi et al. |

FOREIGN PATENT DOCUMENTS

| | | |
|---|---|---|
| JP | 2006-77006 | 3/2006 |
| JP | 2006-176503 | 7/2006 |
| WO | WO 2006/018280 A2 | 2/1923 |
| WO | WO 97/17954 A1 | 5/1997 |
| WO | WO 97/38665 A2 | 10/1997 |
| WO | WO 98/39000 A1 | 9/1998 |
| WO | WO 99/37304 A1 | 7/1999 |
| WO | WO 99/65867 A1 | 12/1999 |
| WO | WO 00/18391 A1 | 4/2000 |
| WO | WO 00/42852 A1 | 7/2000 |
| WO | WO 01/07436 A2 | 2/2001 |
| WO | WO 01/66114 A1 | 9/2001 |
| WO | WO 02/05819 A2 | 1/2002 |
| WO | WO 03/024450 A1 | 3/2003 |
| WO | WO 03/024456 A2 | 3/2003 |
| WO | WO 03/032914 A2 | 4/2003 |
| WO | WO 2003/066581 | 8/2003 |
| WO | WO 03/076400 A1 | 9/2003 |
| WO | WO 03/092606 A2 | 11/2003 |
| WO | WO 2004/010942 A2 | 2/2004 |
| WO | WO 2004/014374 A1 | 2/2004 |
| WO | WO 2004/017950 A1 | 3/2004 |
| WO | WO 2004/034963 A2 | 4/2004 |
| WO | WO 2004/002531 A1 | 7/2004 |
| WO | WO 2005/074535 A2 | 8/2005 |
| WO | WO 2005/087226 A1 | 9/2005 |
| WO | WO 2006/003030 A1 | 1/2006 |
| WO | WO 2006/004201 A1 | 1/2006 |
| WO | WO 2006/034441 A1 | 3/2006 |
| WO | WO 2006/034446 A2 | 3/2006 |
| WO | WO 2006/049880 A2 | 5/2006 |
| WO | WO 2006/065479 A2 | 6/2006 |
| WO | WO 2006/138657 A1 | 12/2006 |
| WO | WO 2007/020888 A1 | 2/2007 |
| WO | WO 2007/027532 A2 | 3/2007 |
| WO | WO 2007/037187 A1 | 4/2007 |
| WO | WO 2007/086584 A1 | 8/2007 |
| WO | WO 2008/045393 A2 | 4/2008 |
| WO | WO 2009/023179 A1 | 2/2009 |
| WO | WO 2009/042444 A2 | 4/2009 |
| WO | WO 2010/077915 A1 | 7/2010 |
| WO | WO 2010/088050 A2 | 8/2010 |
| WO | WO 2010/091409 A1 | 8/2010 |
| WO | WO 2010/119992 A1 | 10/2010 |
| WO | WO 2010/120741 | 10/2010 |
| WO | WO 2011/156532 | 12/2011 |
| WO | WO 2012/025164 | 3/2012 |
| WO | WO 2012/071369 | 5/2012 |
| WO | WO 2012/158844 | 11/2012 |
| WO | WO 2013/166037 | 11/2013 |
| WO | WO 2013/166040 | 11/2013 |
| WO | WO 2013/166041 | 11/2013 |
| WO | WO 2014/151936 | 9/2014 |
| WO | WO 2014/151959 | 9/2014 |
| WO | WO 2014/152013 | 9/2014 |
| WO | WO 2014/152018 | 9/2014 |
| WO | WO 2014/160409 | 10/2014 |

OTHER PUBLICATIONS

Notification of Transmittal of the International Search Report and the Written Opinion of the International Searching Authority, or the Declaration issued Aug. 22, 2014 in connection with PCT/US2014/026523.

International Search Report in connection with PCT/US2014/026818 issued Jul. 18, 2014.

Written Opinion issued Jul. 18, 2014 in connection with PCT/US2014/026818.

Notification of Transmittal of the International Search Report and the Written Opinion of the International Searching Authority, or the Declaration issued Jul. 18, 2014 in connection with PCT/US2014/026818.

International Search Report in connection with PCT/US2014/026730 issued Jul. 21, 2014.

Written Opinion issued Jul. 21, 2014 in connection with PCT/US2014/026730.

Notification of Transmittal of the International Search Report and the Written Opinion of the International Searching Authority, or the Declaration issued Jul. 21, 2014 in connection with PCT/US2014/026730.

International Search Report in connection with PCT/US2014/026699 issued Jul. 18, 2014.

Written Opinion issued Jul. 18, 2014 in connection with PCT/US2014/026699.

Notification of Transmittal of the International Search Report and the Written Opinion of the International Searching Authority, or the Declaration issued Jul. 18, 2014 in connection with PCT/US2014/026699.

Written Opinion issued Sep. 20, 2013 in connection with PCT/US2013/038908.

Written Opinion issued Sep. 27, 2013 in connection with PCT/US2013/038905.

Written Opinion issued Sep. 24, 2013 in connection with PCT/US2013/038910.

Nov. 8, 2010 CAS Search Report.

Notification Concerning Transmittal of International Preliminary Report on Patentability (Chapter I of the Patent Cooperation Treaty), including an International Preliminary Report on Patentability and Written Opinion of the International Searching Authority, mailed Jun. 6, 2013 by The International Bureau of WIPO in connection with PCT International Application No. PCT/US2011/061763, filed Nov. 22, 2011.

Motani et al. (2009). Identification and characterization of a non-retinoid ligand for retinol-binding protein 4 which lowers serum retinol-binding protein 4 levels in vivo. *Journal of Biological Chemistry*, 284(12), 7673-7680.

Petrukhin. (2007). New therapeutic targets in atrophic age-related macular degeneration. *Expert Opin Ther Targets*, 11(5), 625-639.

Sparrow et al. (2010). Phospholipid meets all-trans-retinal: the making of RPE bisretinoids. *J Lipid Res*, 51(2), 247-261.

Elenewski & Hackett (2010). Free energy landscape of the retinol/serum retinol binding protein complex: a biological host-guest system. *J Phys Chem B*, 114(34), 11315-11322.

Sharif et al. (2009). Time-resolved fluorescence resonance energy transfer and surface plasmon resonance-based assays for retinoid and transthyretin binding to retinol-binding protein 4. *Anal Biochem*, 392(2), 162-168.

Wu et al. (2009). Novel lipofuscin bisretinoids prominent in human retina and in a model of recessive Stargardt disease. *J Biol Chem*, 284(30), 20155-20166.

Sparrow et al. (2010). Interpretations of fundus autofluorescence from studies of the bisretinoids of the retina. *Invest Ophthalmol Vis Sci*, 51(9), 4351-4357.

Notification of Transmittal of the International Search Report and the Written Opinion of the International Searching Authority, or the Declaration, including an International Search Report and Written Opinion of the International Searching Authority, mailed May 29,

(56) References Cited

OTHER PUBLICATIONS 2012 in connection with PCT International Application No. PCT/US2011/061763, filed Nov. 22, 2011.
International Search Report in connection with PCT/US2011/061763 issued May 29, 2012.
International Preliminary Report on Patentability in connection with PCT/US2011/061763 issued May 29, 2012.
Written Opinion issued May 29, 2012 in connection with PCT/US2011/061763.
Notification of Transmittal of the International Search Report and the Written Opinion of the International Searching Authority, or the Declaration issued May 29, 2012 in connection with PCT/US2011/061763.
International Search Report in connection with PCT/US2013/038906 issued Sep. 20, 2013.
Notification of Transmittal of the International Search Report and the Written Opinion of the International Searching Authority, or the Declaration issued Sep. 20, 2013 in connection with PCT/US2013/038908.
International Search Report in connection with PCT/US2013/038905 issued Sep. 27, 2013.
Notification of Transmittal of the International Search Report and the Written Opinion of the International Searching Authority, or the Declaration issued Sep. 27, 2013 in connection with PCT/US2013/038905.
International Search Report in connection with PCT/US2013/038910 issued Sep. 24, 2013.
Notification of Transmittal of the International Search Report and the Written Opinion of the International Searching Authority, or the Declaration issued Sep. 24, 2013 in connection with PCT/US2013/038910.
Extended European Search Report issued Aug. 19, 2014 in connection with European Patent Application No. 11842785.5.
Bourgault, S. et al. (2011) Mechanisms of transthyretin cardiomyocyte toxicity inhibition by resveratrol analogs.Biochem Biophys Res Commun. 410(4):707-13.

* cited by examiner

**all-*trans*-retinal dimer-phosphatidylethanolamine**

**all-*trans*-retinal dimer**

NON-RETINOID RBP4 ANTAGONIST FOR TREATMENT OF AGE-RELATED MACULAR DEGENERATION AND STARGARDT DISEASE

This application is a §371 national stage of PCT International Application No. PCT/US2011/061763, filed Nov. 22, 2011, claiming the benefit of U.S. Provisional Application No. 61/416,961, filed Nov. 24, 2010, the contents of each of which are hereby incorporated by reference in its entirety.

This invention was made with government support under grant numbers NS067594 and EY012951 awarded by the National Institutes of Health. The government has certain rights in the invention.

Throughout this application, certain publications are referenced in parenthesis. Full citations for these publications may be found immediately preceding the claims. The disclosures of these publications in their entireties are hereby incorporated by reference into this application in order to describe more fully the state of the art to which this invention relates.

BACKGROUND OF THE INVENTION

Age-related macular degeneration (AMD) is the leading cause of blindness in developed countries. It is estimated that 62.9 million individuals worldwide have the most prevalent atrophic (dry) form of AMD; 8 million of them are Americans. Due to increasing life expectancy and current demographics this number is expected to triple by 2020. There is currently no FDA-approved treatment for dry AMD. Given the lack of treatment and high prevalence, development of drugs for dry AMD is of upmost importance. Clinically, atrophic AMD represents a slowly progressing neurodegenerative disorder in which specialized neurons (rod and cone photoreceptors) die in the central part of the retina called macula (1). Histopathological and clinical imaging studies indicate that photoreceptor degeneration in dry AMD is triggered by abnormalities in the retinal pigment epithelium (RPE) that lies beneath photoreceptors and provides critical metabolic support to these light-sensing neuronal cells. Experimental and clinical data indicate that excessive accumulation of cytotoxic autofluorescent lipid-protein-retinoid aggregates (lipofuscin) in the RPE is a major trigger of dry AMD (2-9). In addition to AMD, dramatic accumulation of lipofuscin is the hallmark of Stargardt Disease (STGD), an inherited form of juvenile-onset macular degeneration. The major cytotoxic component of RPE lipofuscin is pyridinium bisretinoid A2E (FIG. 1). Additional cytotoxic bisretinoids are isoA2E, atRAL di-PE, and A2-DHP-PE (40, 41).

A2E is a product of condensation of all-trans retinaldehyde with phosphatidyl-ethanolamine which occurs in the retina in a non-enzymatic manner and, as illustrated in FIG. 4, can be considered a by-product of a properly functioning visual cycle (10). Light-induced isomerization of 11-cis retinaldehyde to its all-trans form is the first step in a signaling cascade that mediates light perception. The visual cycle is a chain of biochemical reactions that regenerate visual pigment (11-cis retinaldehyde conjugated to opsin) following exposure to light.

As cytotoxic bisretinoids are formed during the course of a normally functioning visual cycle, partial pharmacological inhibition of the visual cycle may represent a treatment strategy for dry AMD and other disorders characterized by excessive accumulation of lipofuscin (25-27, 40, 41).

SUMMARY OF THE INVENTION

The present invention relates to a method for treating bisretinoid-mediated macular degeneration in a mammal afflicted therewith comprising administering to the mammal an effective amount of a compound having the structure:

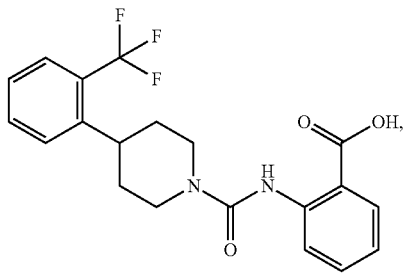 [SMILES: O=C(O)c1ccccc1NC(=O)N1CCC(c2ccccc2C(F)(F)F)CC1]

an ester or a pharmaceutically acceptable salt thereof.

The present invention also relates to a method for determining whether a molecule is an antagonist of retinol-induced RBP4-TTR interaction.

In one embodiment, the method comprises:
i) incubating RBP4 tagged with a donor or acceptor fluorophore with TTR tagged with a donor or acceptor fluorophore and retinol, wherein when RBP4 is tagged with a donor fluorophore then TTR is tagged with an acceptor fluorophore, and when RBP4 is tagged with an acceptor fluorophore then TTR is tagged with an acceptor fluorophore,
ii) determining the ratio of fluorescence of wavelengths for the donor and acceptor fluorophores within the mixture of i) upon excitation of the donor fluorophore by an energy source,
iii) incubating the molecule with the fluorophore tagged RBP4, fluorophore tagged TTR, and retinol of i),
iv) determining the ratio of fluorescence of wavelengths for the donor and acceptor fluorophores within the mixture of iii) upon excitation of the donor fluorophore by an energy source,
v) determining whether the fluorescence ratio in step iv) is less than the fluorescence ratio in step ii), In this embodiment, a fluorescence ratio in step iv) that is less than step ii) indicates that the molecule is an antagonist of retinol-induced RBP4-TTR interaction.

DETAILED DESCRIPTION OF THE INVENTION

Figure 1:
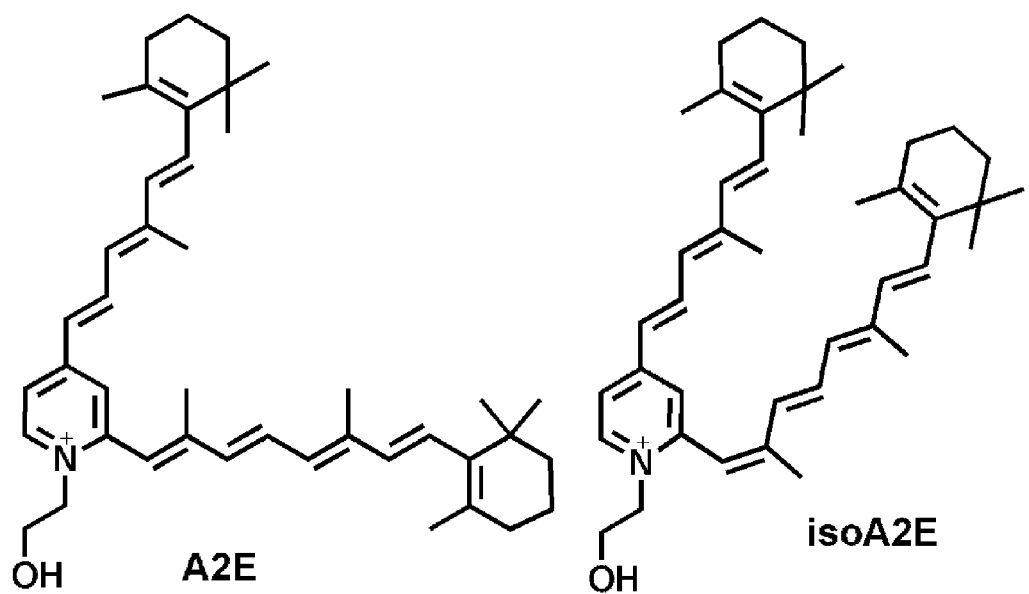
FIG. 1. Structure of bisretinoid A2E, a cytotoxic component of retinal lipofuscin.

The present invention relates to a method for treating bisretinoid-mediated macular degeneration in a mammal afflicted therewith comprising administering to the mammal an effective amount of a compound having the structure:

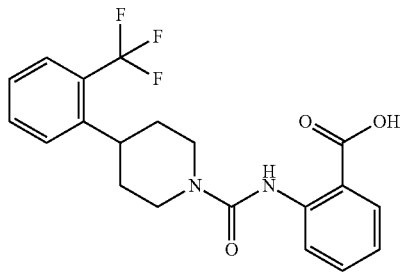 [SMILES: O=C(O)c1ccccc1NC(=O)N1CCC(c2ccccc2C(F)(F)F)CC1]

termed Compound 1 herein, an ester or a pharmaceutically acceptable salt thereof.

The amount of Compound 1 may be effective to lower the serum concentration of RBP4 in the mammal.

In some embodiments of the invention, the amount of Compound 1 may be effective to lower the retinal concentration of a bisretinoid in lipofuscin in the mammal. In some embodiments, the bisretinoid is A2E. In some embodiments the bisretinoid is isoA2E. In some embodiments the bisretinoid is A2-DHP-PE. In some embodiments the bisretinoid is atRAL di-PE.

In preferred embodiments, bisretinoid-mediated macular degeneration may be Age-Related Macular Degeneration or Stargardt Disease.

The bisretinoid-mediated macular degeneration may comprise the accumulation of lipofuscin deposits in the retinal pigment epithelium.

The present invention also relates to a method for determining whether a molecule is an antagonist of retinol-induced RBP4-TTR interaction.

In one embodiment, the method comprises:
i) incubating RBP4 tagged with a donor or acceptor fluorophore with TTR tagged with a donor or acceptor fluorophore and retinol, wherein when RBP4 is tagged with a donor fluorophore then TTR is tagged with an acceptor fluorophore, and when RBP4 is tagged with an acceptor fluorophore then TTR is tagged with an acceptor fluorophore,
ii) determining the ratio of fluorescence of wavelengths for the donor and acceptor fluorophores within the mixture of i) upon excitation of the donor fluorophore by an energy source,
iii) incubating the molecule with the fluorophore tagged RBP4, fluorophore tagged TTR, and retinol of i),
iv) determining the ratio of fluorescence of wavelengths for the donor and acceptor fluorophores within the mixture of iii) upon excitation of the donor fluorophore by an energy source,
v) determining whether the fluorescence ratio in step iv) is less than the fluorescence ratio in step ii), In this embodiment, a fluorescence ratio in step iv) that is less than step ii) indicates that the molecule is an antagonist of retinol-induced RBP4-TTR interaction. In further embodiments, the method also comprises the step of determining whether the molecule reduces the level of bisretinoid lipofuscin in a cell. The cell may be a retinal pigment epithelial cell.

The compound 2(4-(2-(trifluoromethyl)phenyl)piperidine-1-carboxamido)benzoic acid has the structure:

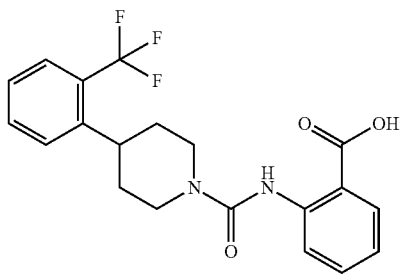 [SMILES: O=C(O)c1ccccc1NC(=O)N1CCC(c2ccccc2C(F)(F)F)CC1]

termed "Compound 1" herein, and was obtained from Sigma (Sigma-Aldrich Corp., St. Louise Mo., USA, Catalogue No. A3111). Compound 1, has also been called A1120 and may be made by the following techniques described in Motani et al., 2009 as follows:

A solution of methyl 2-isocyanatobenzoate (10.00 g, 56.4 mmol) in tetrahydrofuran (30 ml) was slowly added to a solution of 4-(2-(trifluoromethyl)phenyl)piperidine hydrochloride (14.3 g, 53.8 mmol, Sigma) and triethylamine 99% (8.99 ml, 64.5 mmol) in tetrahydrofuran (120 ml) at 0° C. The mixture was removed from the cooling bath and stirred at room temperature for 15 min, at which time LC/MS analysis indicated that the reaction was complete. EtOH (75 ml) and aqueous LiOH (2N, 95 ml) were then added, and the solution was stirred for 6 h at room temperature. Subsequently, aqueous HCl (2N, 150 ml) was added, and the resulting mixture was extracted with EtOAc (2×600 ml). The EtOAc extract was dried over MgSO4 and concentrated to an off-white solid. Recrystallization from EtOAc yielded 14.0 g (66%) of 2-(4-(2-(trifluoromethyl)phenyl)piperidine-1-carboxamido) benzoic acid as a white solid, which was homogeneous by analytical high-performance liquid chromatography (>99%).

Figure 2:
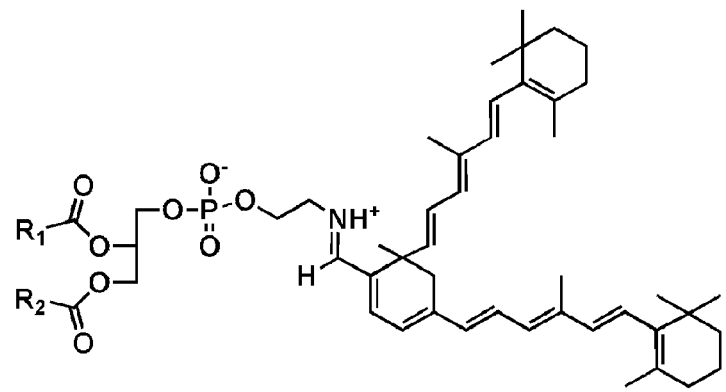
FIG. 2. Structure of bisretinoid atRAL di-PE (all-trans-retinal dimer-phosphatidyl ethanolamine), a cytotoxic component of retinal lipofuscin. R1 and R2 refer to various fatty acid constituents.
Figure 2:
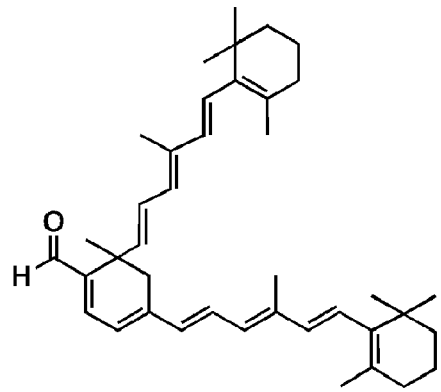
Figure 3:
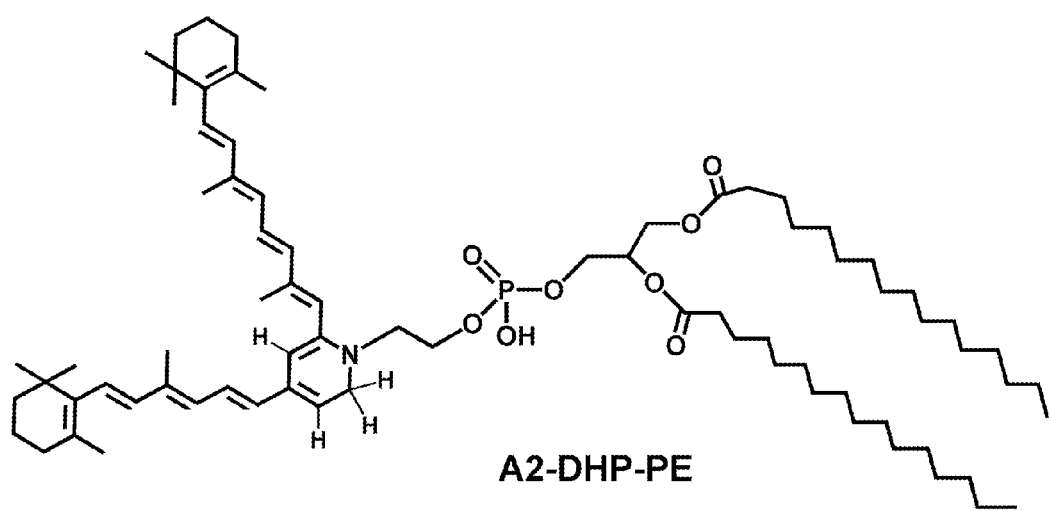
FIG. 3. Structure of bisretinoid A2-DHP-PE, a cytotoxic component of retinal lipofuscin.

As used herein, "bisretinoid lipofuscin" is lipofuscin containing a cytotoxic bisretinoid. Cytotoxic bisretinoids include but are not necessarily limited to A2E, isoA2E, atRAL di-PE, and A2-DHP-PE (FIG. 1-3).

As used herein, the description "pharmaceutically active" is used to characterize a substance, compound, or composition suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department of Health and Human Services, 30th edition, 2010), which are hereby incorporated by reference.

Ester derivatives of Compound 1 may be generated from its carboxylic acid group in accordance with the present invention using standard esterification reactions and methods readily available and known to those having ordinary skill in the art of chemical synthesis. Ester derivatives may serve as pro-drugs that can be converted into Compound 1 by serum esterases.

Compound 1 may be in a salt form. As used herein, a "salt" is a salt of the instant compound which has been modified by making acid or base salts of the compounds. In the case of the use of Compound 1 for treatment of bisretinoid-mediated macular degeneration, the salt is pharmaceutically acceptable. Examples of pharmaceutically acceptable salts include, but are not limited to, mineral or organic acid salts of basic residues such as amines. The term "pharmaceutically acceptable salt" in this respect, refers to the relatively non-toxic, inorganic and organic base addition salts of Compound 1. These salts can be prepared in situ during the final isolation and purification of Compound 1, or by separately reacting purified Compound 1 in its free acid form with a suitable organic or inorganic base, and isolating the salt thus formed.

As used herein, "treating" means slowing, stopping, or preventing the progression of a disease. An embodiment of "treating bisretinoid-mediated macular degeneration" is delaying or preventing the onset, progression, or mitigating severity of vision loss.

A "fluorophore" is a molecule which absorbs electromagnetic energy at one wavelength and re-emits energy at another wavelength. A fluorophore may be a molecule or part of a molecule including fluorescent dyes and proteins. Additionally, a fluorophore may be chemically, genetically, or otherwise connected or fused to another molecule to produce a molecule that has been "tagged" with the fluorophore. Examples of fluorophores include but are not limited to lanthanides, europium, terbium, XL665, d2, quantum dots, green fluorescent protein, red fluorescent protein, yellow fluorescent protein, fluorescein, rhodamine, eosin, Texas red, cyanine, indocarbocyanine, ocacarbocyanine, thiacarbocyanine, merocyanine, pyridyloxadole, benzoxadiazole, cascade blue, nile red, oxazine 170, acridine orange, proflavin, auramine, malachite green crystal violet, porphine phtalocyanine, and bilirubin.

As used herein, a "donor fluorophore" is a fluorophore whose emission spectrum is within the absorbance spectrum of an acceptor fluorophore, so that when excited by an electromagnetic energy source, the re-emitted energy of the donor fluorophore is sufficient to be absorbed by, and then re-emitted by the acceptor fluorophore when the two fluorophores are within 90 Å of each other. Examples of a donor fluorophore include but are not limited to Europium cryptate, green fluorescent protein, and yellow fluorescent protein.

As used herein, an "acceptor fluorophore" is a fluorophore whose absorption spectrum is within the emission spectrum of a donor fluorophore, so that it is capable of absorbing and re-emitting the re-emitted energy of a donor fluorophore that has been excited by electromagnetic energy when the two fluorophores are within 90 Å of each other. Examples of acceptor fluorophores include but are not limited to XL665 and d2 Europium cryptate.

As used herein, an "energy source" is a source of electromagnetic energy capable of exciting a fluorophore. Examples of energy sources include but are not limited to flash lamps, fluorescent bulbs, and fluorometer lasers.

Compound 1 may be administered in various forms, including those detailed herein. The treatment with the compound may be a component of a combination therapy or an adjunct therapy, i.e. the mammal in need of the drug is treated or given another drug for the disease in conjunction with Compound 1. This combination therapy can be sequential therapy where the mammal is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the mammal. The carrier may be liquid or solid and is selected with the planned manner of administration in mind. Liposomes are also a pharmaceutically acceptable carrier.

The dosage of Compound 1 administered in treatment will vary depending upon factors such as the pharmacodynamic characteristics of Compound 1 and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of Compound 1 may comprise Compound 1 alone, or mixtures of Compound 1 with additional compounds used to treat lipofuscin-mediated macular degeneration. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection or other methods, into the eye, all using dosage forms well known to those of ordinary skill in the pharmaceutical arts.

Compound 1 can be administered in a mixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone but are generally mixed with a pharmaceutically acceptable carrier. This carrier can be a solid or liquid, and the type of carrier is generally chosen based on the type of administration being used. In one embodiment the carrier can be a monoclonal antibody. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Specific examples of pharmaceutical acceptable carriers and excipients that may be used to formulate oral dosage forms of the present invention are described in U.S. Pat. No. 3,903,297, issued Sep. 2, 1975. Techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Compound 1 can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines. The compounds may be administered as components of tissue-targeted emulsions.

Compound 1 may also be coupled to soluble polymers as targetable drug carriers or as a prodrug. Such polymers include polyvinylpyrrolidone, pyran copolymer, polyhydroxylpropylmethacrylamide-phenol, polyhydroxyethylasparta-midephenol, or polyethyleneoxide-polylysine substituted with palmitoyl residues. Furthermore, Compound 1 may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Compound 1 can be administered orally in solid dosage forms, such as capsules, tablets, and powders, or in liquid dosage forms, such as elixirs, syrups, and suspensions. It can also be administered parentally, in sterile liquid dosage forms.

Gelatin capsules may contain Compound 1 and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For oral administration in liquid dosage form, Compound 1 may be combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

Compound 1 may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials to make them compatible with the type of injection or delivery system chosen.

The Compound 1 and compositions thereof of the invention can be coated onto stents for temporary or permanent implantation into the cardiovascular system of a subject.

The compounds and compositions of the present invention are useful for the prevention and treatment of lipofuscin-mediated macular degeneration.

This invention will be better understood by reference to the Examples which follow, but those skilled in the art will readily appreciate that the specific experiments detailed are only illustrative of the invention as described more fully in the claims which follow thereafter.

EXAMPLES

Example 1

TR-FRET Assay for Antagonists of Retinol-Induced RBP4-TTR Interaction

Figure 7:
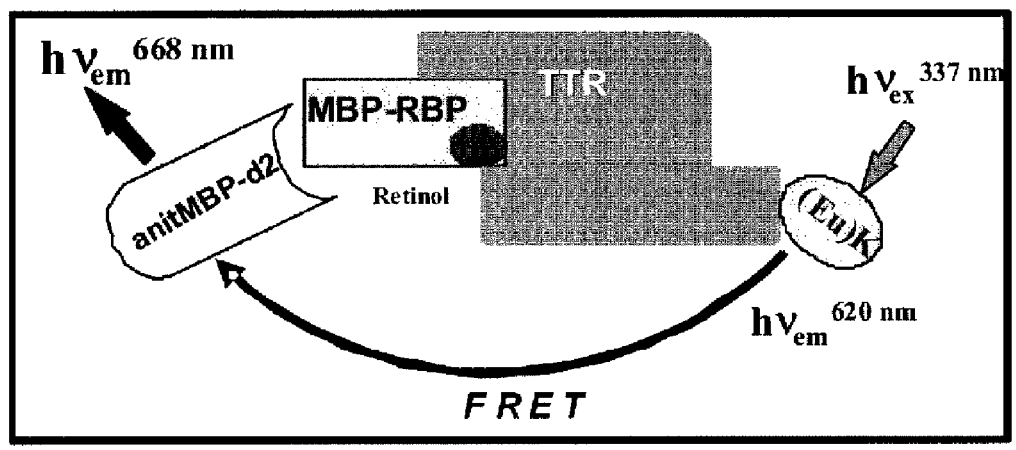
FIG. 7. Schematic depiction of the HTRF-based assay format for characterization of RBP4 antagonists disrupting retinol-induced RBP4-TTR interaction.

TR-FRET (Time-Resolved Fluorescence Resonance Energy Transfer) is an assay format that can be used in characterization of compounds affecting protein-protein interactions (31-33). The HTRF (Homogeneous Time-Resolved Fluorescence) variant of TR-FRET is the most advanced as it has improved light capturing due to the use of Eu3+ cryptates. In the presence of retinol, RBP4-TTR interaction induces FRET that can be registered as increased ratio of 668/620 fluorescence signals. Binding of a desired RBP4 antagonist displaces retinol and induces hindrance for RBP4-TTR interaction resulting in the decreased FRET signal (FIG. 7).

Figure 8:
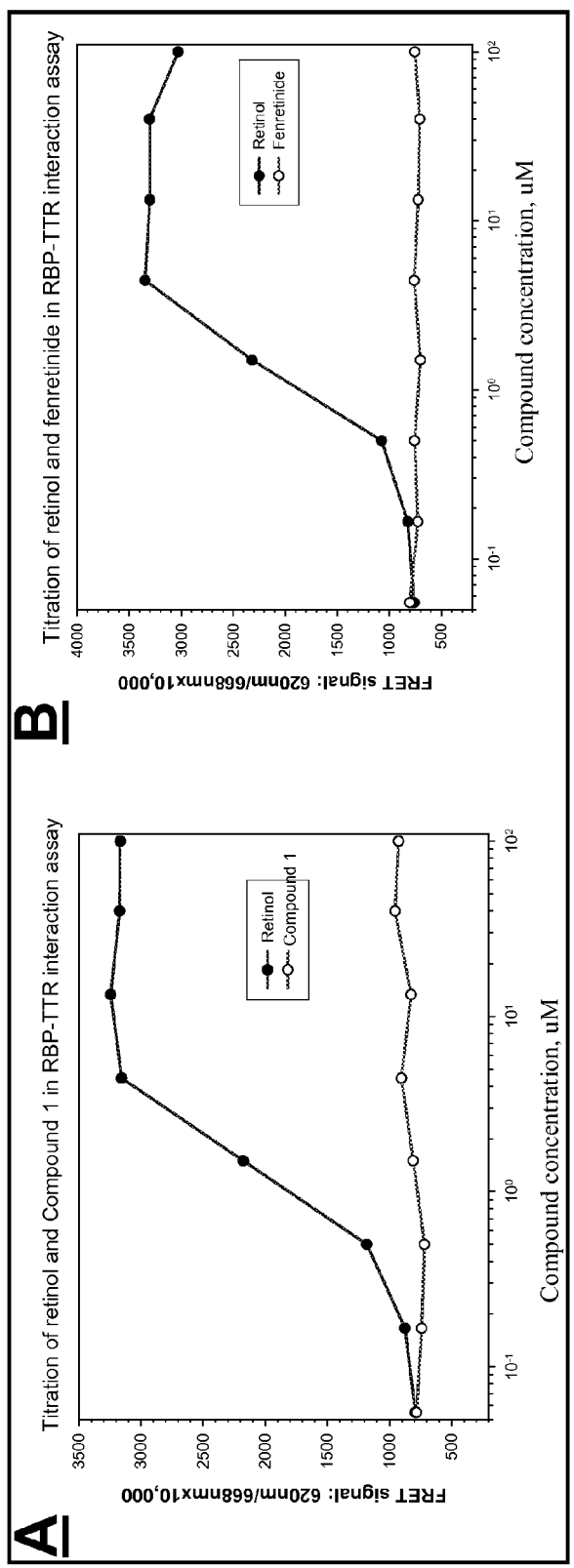
FIG. 8. Dose titrations of all-trans retinol (panels A and B, blue), Compound 1 (red, A), and fenretinide (red, B) in the HTRF-based RBP4-TTR interaction assay.
Figure 9:
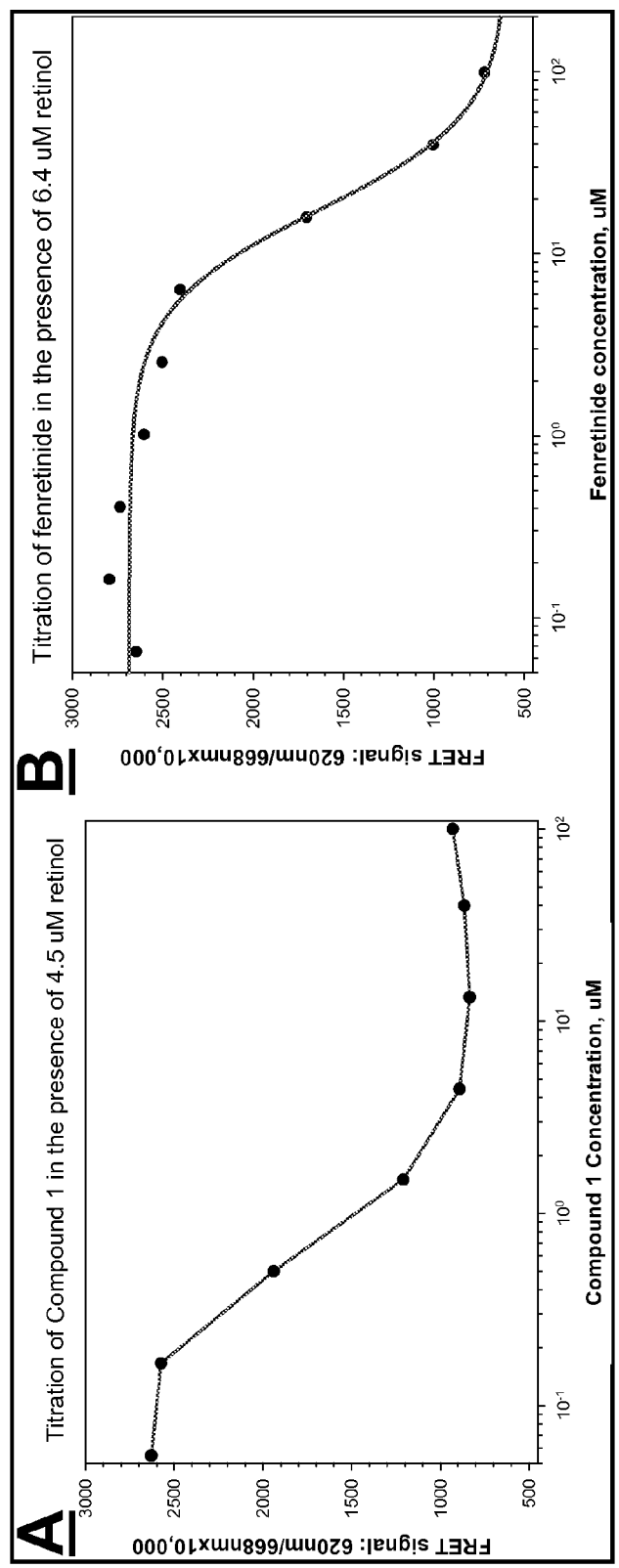
FIG. 9. Dose titrations of Compound 1 and fenretinide in the presence of all-trans retinol in the HTRF-based RBP4-TTR interaction assay.
Figure 10:
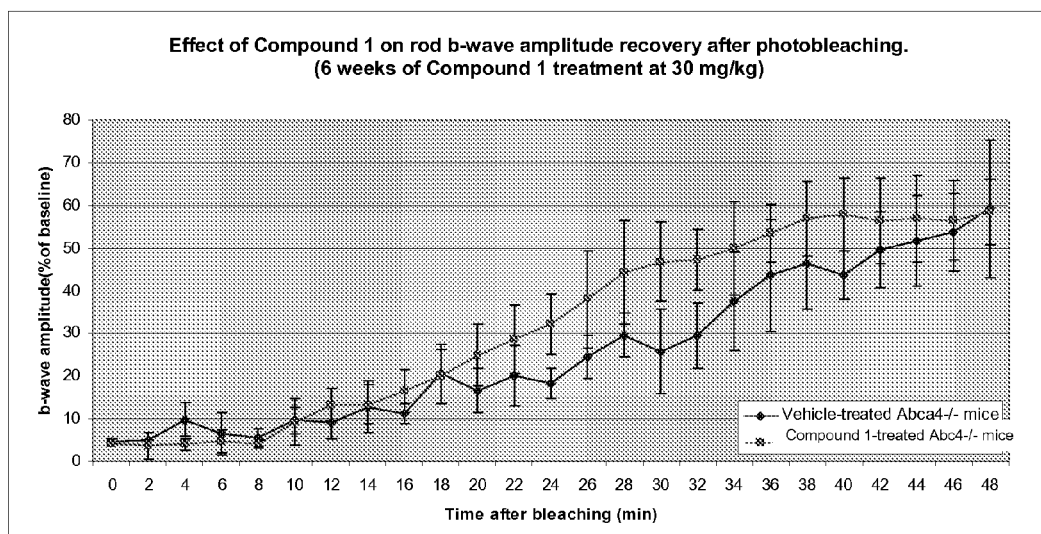
FIG. 10. Compound 1 does not reduce ERG b-wave after photobleaching.

The inventors developed an assay using *E. coli*-expressed MBP-tagged RBP4 and commercially available TTR labeled directly with Eu3+ cryptate. In addition to MBP-RBP4 and Eu3+ (K)-TTR, a detector reagent anti-MBP-d2 was present in the mix. The assay was first optimized in the agonist mode; sensitivity and dynamic range of the assay was first mode in respect to RBP4, TTR and detection reagent concentrations. In order to determine the optimum concentration of all-trans retinol stimulating the RBP4-TTR interaction the inventors performed eight-point titration retinol titrations along with titrations of Compound 1 and fenretinide (FIG. 8). The inventors demonstrated that all-trans retinol stimulates RBP4-TTR interaction in a dose dependent manner (FIG. 8) with EC50 of ~1.2 µM. As expected, RBP4 antagonists Compound 1 and fenretinide did not induce RBP4-TTR interaction (FIG. 8).

Given that retinol is present in serum at micromolar concentrations and taking into account the results of retinol titrations, the inventors converted the assay to the antagonist mode by testing fixed concentration of retinol within the 1-10 µM range and using the saturating 40 µM concentration of antagonists (fenretinide and Compound 1). The optimum retinol concentration in the antagonist mode in regard of assay sensitivity and dynamic range was found to be in the 4.5-6.5 µM range. The inventors conducted titrations of Compound 1 and fenretinide in the presence of retinol in order to characterize our starting compounds in the primary assay and prove that the assay is suitable for characterization of RBP4 antagonists (FIG. 8).

The two compounds, Compound 1 and fenretinide, antagonized the retinol-induced RBP4-TTR interaction with EC50's in the µM range (2.2 µM for Compound 1 and 17.3 µM for fenretinide).

Example 2

Compound 1 Efficacy in a Mammalian Model

Figure 11:
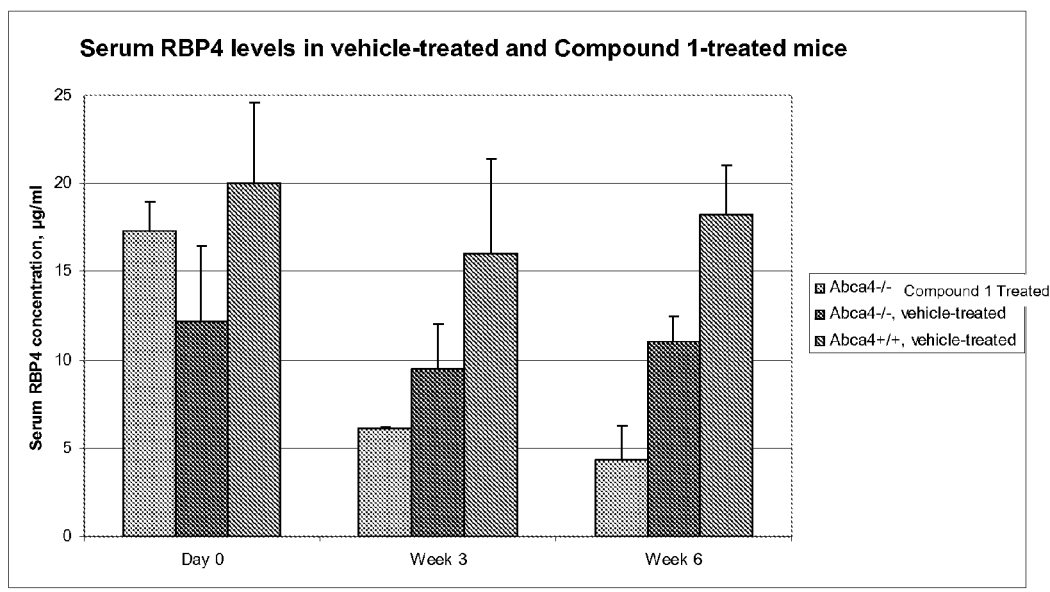
FIG. 11. Reduction in serum RBP4 in response to Compound 1 treatment.
Figure 12:
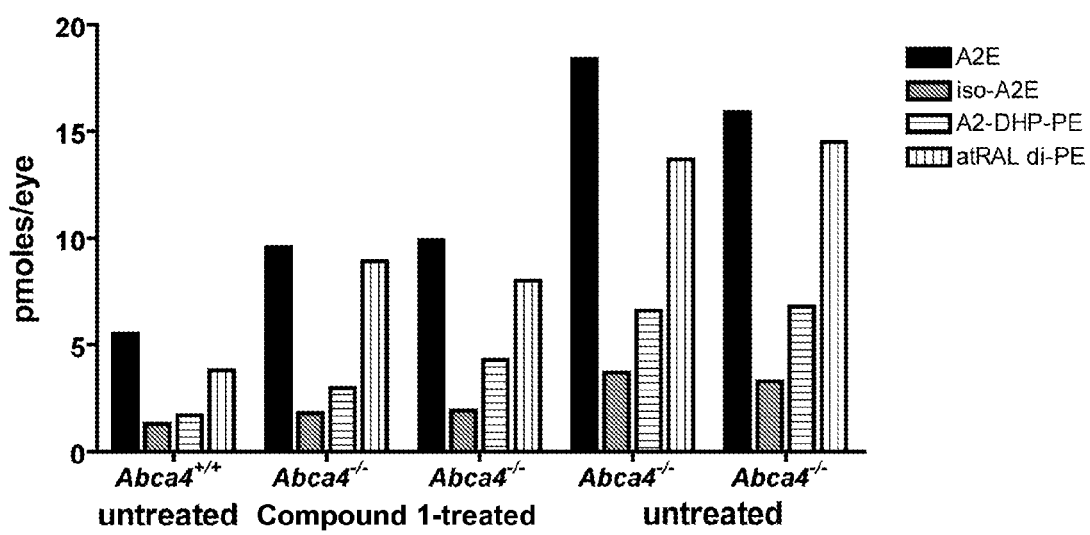
FIG. 12. Reduction of toxin bisretinoids by Compound 1.

The effectiveness of Compound 1 was tested in wild-type and Abca4−/− mice. The Abca4−/− mouse model manifests accelerated accumulation of lipofuscin in the RPE and is considered a preclinical efficacy model for a drug reducing lipofuscin accumulation. Compound 1 was orally dosed for 3 weeks at 30 mg/kg. There was approximately a 70% reduction in the serum RBP4 level in treated animals (FIG. 11). Additionally, the inventors discovered that that the levels of A2E/isoA2E were reduced by approximately 50% in treated mice (FIG. 12). The levels of A2-DHP-PE and atRAL di-PE were also reduced. These preclinical efficacy data show that Compound 1 is a potential small molecule treatment for dry AMD and Stargardt disease.

Tissue Extraction and HPLC Analysis of Bisretinoids

Abca4/Abcr null mutant mice (albino) homozygous for Rpe65-Leu450 are bred genotyped and housed. Posterior eyecups of mice and RPE/choroids harvested from human donor eyes (National Disease Research Interchange, Philadelphia Pa.) are homogenized in phosphate buffered saline (PBS) using a glass tissue grinder and extracted in chloroform/methanol (2:1). Extracts are subsequently filtered through cotton and passed through a reverse phase cartridge (C8 Sep-Pak, Millipore) with 0.1% TFA (Aldrich Chemical Company, Milwaukee, Wis.) in methanol. After evaporation of solvent under argon gas, the extract is dissolved in 50% methanolic chloroform containing 0.1% TFA. An Alliance system (Waters, Corp, Milford, Mass.) equipped with 2695 Separation Module, 2996 Photodiode Array Detector, a 2475 Multi λ Fluorescence Detector and operating with Empower® software is used for HPLC analysis. An Atlantis® dC18 column (3 µm, 4.6×150 mm, Waters, USA) and a Delta Pak® C4 column (5 µm, 3.9×150 mm, Waters, USA) are employed. Gradients of water and acetonitrile (Fisher, Fair Lawn, N.J.) with 0.1% of TFA are used for mobile phase; details are provided in figure legends. HPLC quantification is carried out using the Empower® software to determine peak areas. Detection by photodiode array is set at 430 and 490 nm. Molar quantity per murine eye is determined using calibration curves constructed from known concentrations of purified external standards and by normalizing to the ratio of the HPLC injection volume (10 µL) versus total extract volume.

DISCUSSION

Serum RBP4 as a Drug Target for Pharmacological Inhibition of the Visual Cycle

Figure 4:
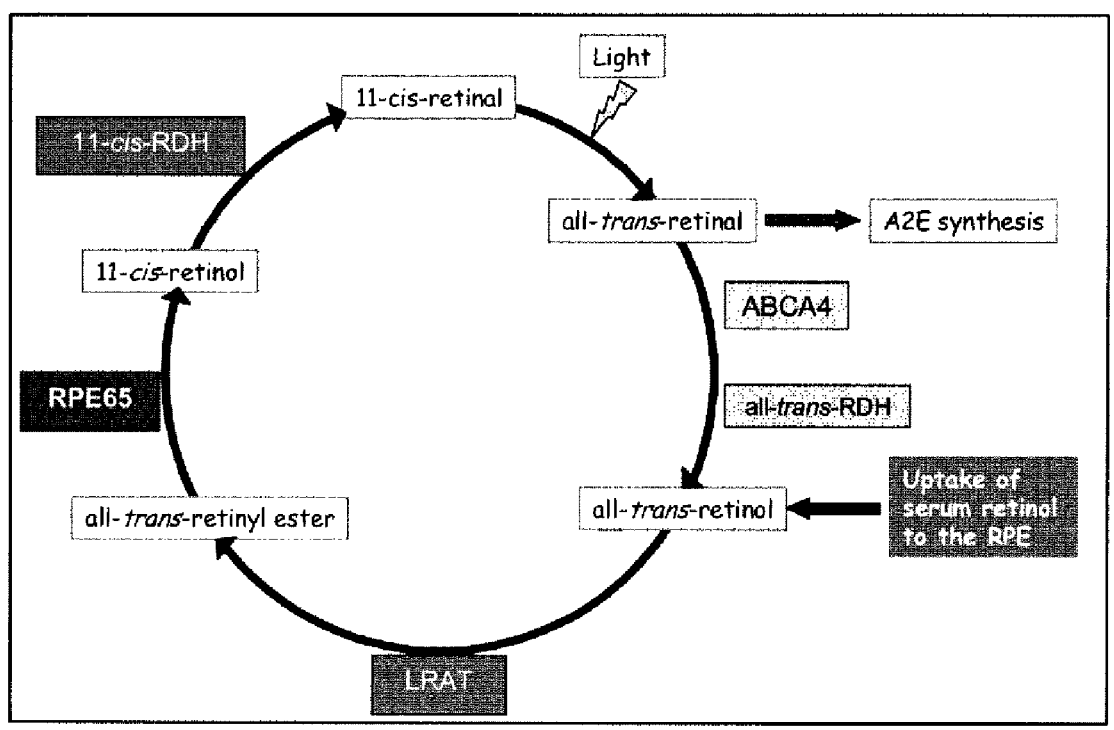
FIG. 4. Visual cycle and biosynthesis of A2E. A2E biosynthesis begins when a portion of all-trans-retinal escapes the visual cycle (yellow box) and non-enzymatically reacts with phosphatidyl-ethanolamine forming the A2E precursor, A2-PE. Uptake of serum retinol to the RPE (gray box) fuels the cycle.
Figure 5:
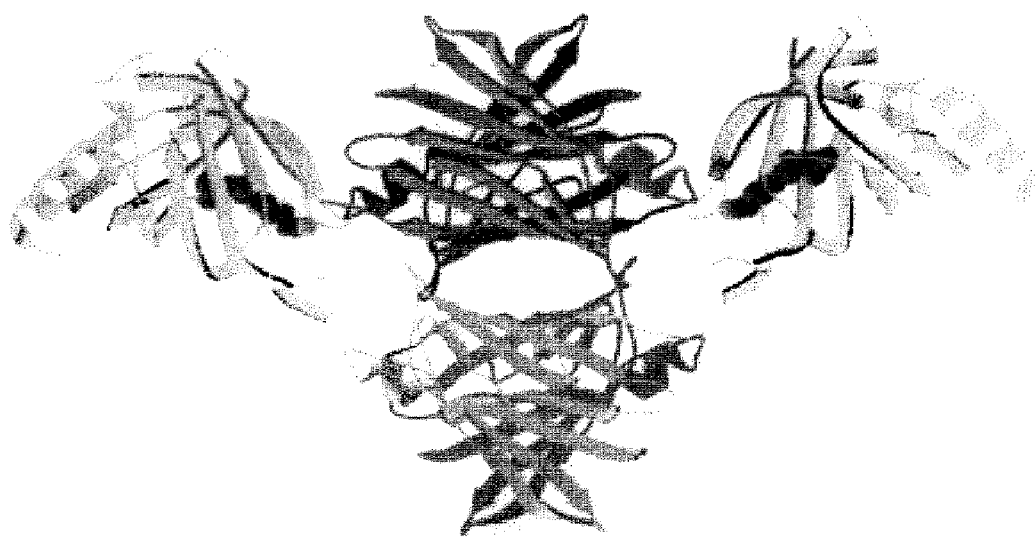
FIG. 5. Three-dimensional structure of the RBP4-TTR-retinol complex. Tetrameic TTR is shown in blue, light blue, green and yellow. RBP is shown in red and retinol is shown in gray (28).
Figure 6:
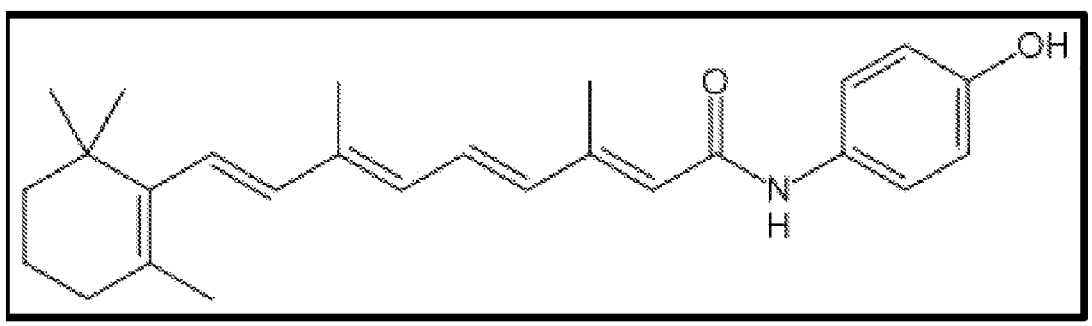
FIG. 6. Structure of fenretinide, [N-(4-hydroxy-phenyl) retinamide, 4HRP], a retinoid RBP4 antagonist.

As rates of the visual cycle and A2E production in the retina depend on the influx of all-trans retinol from serum to the RPE (FIG. 4), it has been suggested that partial pharmacological down-regulation of serum retinol may represent a target area in dry AMD treatment (11). Serum retinol is bound to retinol-binding protein (RBP4) and maintained in circulation as a tertiary complex with RBP4 and transthyretin (TTR)—FIG. 5. Without interacting with TTR, the RBP4-retinol complex is rapidly cleared from circulation due to glomerular filtration. Additionally, formation of the RBP4-TTR-retinol complex is required for receptor-mediated all-trans retinol uptake from serum to the retina.

RBP4 represents an attractive drug target for indirect pharmacological inhibition of the visual cycle and A2E formation. Retinol-binding site on RBP4 is sterically proximal to the interface mediating the RBP4-TTR interaction. Retinol antagonists competing with serum retinol for binding to RBP4 while blocking the RBP4-TTR interaction would reduce serum RBP4 and retinol levels which would lead to reduced uptake of retinol to the retina. The outcome would be visual cycle inhibition with subsequent reduction in the A2E synthesis.

A synthetic retinoid called fenretinide [N-(4-hydroxy-phenyl)retinamide, 4HRP] previously considered as a cancer treatment (29) was found to bind to RBP4, displace all-trans retinol from RBP4 (13), and disrupt the RBP4-TTR interaction (13,14).

Fenretinide was shown to reduce serum RBP4 and retinol (15), inhibit ocular all-trans retinol uptake and slow down the visual cycle (11). Importantly, fenretinide administration reduced A2E production in an animal model of excessive bisretinoid accumulation, Abca4−/− mice (11). Pre-clinical experiments with fenretinide validated RBP4 as a drug target for dry AMD. However, fenretinide is non-selective and toxic. Independent of its activity as an antagonist of retinol binding to RBP4, fenretinide is an extremely active inducer of apoptosis in many cell types (16-19), including the retinal pigment epithelium cells (20). It has been suggested that fenretinide's adverse effects are mediated by its action as a ligand of a nuclear receptor RAR (21-24). Additionally, similar to other retinoids, fenretinide is teratogenic.

Disclosed herein is the ophthalmic use of the small molecule Compound 1 or esters or salts thereof. Compound 1, 2(4-(2-(trifluoromethyl)phenyl)piperidine-1-carboxamido) benzoic acid, is a non-retinoid RBP4 antagonist. Compound 1 was originally developed as an anti-diabetic agent (12). However, its administration did not improve insulin sensitivity in mouse diabetes models.

REFERENCES

1. Petrukhin K. New therapeutic targets in atrophic age-related macular degeneration. Expert Opin. Ther. Targets. 2007, 11(5): 625-639
2. C. Delori, D. G. Goger and C. K. Dorey, Age-related accumulation and spatial distribution of lipofuscin in RPE of normal subjects. Investigative Ophthalmology and Visual Science 42 (2001), pp. 1855-1866
3. F. C. Delori, RPE lipofuscin in ageing and age-related macular degeneration. In: G. Coscas and F. C. Piccolino, Editors, Retinal Pigment Epithelium and Macular Disease (Documenta Ophthalmologica) vol. 62, Kluwer Academic Publishers, Dordrecht, The Netherlands (1995), pp. 37-45.
4. C. K. Dorey, G. Wu, D. Ebenstein, A. Garsd and J. J. Weiter, Cell loss in the aging retina. Relationship to lipofuscin accumulation and macular degeneration. Investigative Ophthalmology and Visual Science 30 (1989), pp. 1691-1699.
5. L. Feeney-Burns, E. S. Hilderbrand and S. Eldridge, Aging human RPE: morphometric analysis of macular, equatorial, and peripheral cells. Investigative Ophthalmology and Visual Science 25 (1984), pp. 195-200.
6. F. G. Holz, C. Hellman, S. Staudt, F. Schutt and H. E. Volcker, Fundus autofluorescence and development of geographic atrophy in age-related macular degeneration. Investigative Ophthalmology and Visual Science 42 (2001), pp. 1051-1056.
7. F. G. Holz, C. Bellmann, M. Margaritidis, F. Schutt, T. P. Otto and H. E. Volcker, Patterns of increased in vivo fundus autofluorescence in the junctional zone of geographic atrophy of the retinal pigment epithelium associated with age-related macular degeneration. Graefe's Archive for Clinical and Experimental Ophthalmology 237 (1999), pp. 145-152.
7. A. von Rückmann, F. W. Fitzke and A. C. Bird, Fundus autofluorescence in age-related macular disease imaged with a laser scanning ophthalmoscope. Investigative Ophthalmology and Visual Science 38 (1997), pp. 478-486.
9. F. G. Holz, C. Hellman, S. Staudt, F. Schutt and H. E. Volcker, Fundus autofluorescence and development of geographic atrophy in age-related macular degeneration. Investigative Ophthalmology and Visual Science 42 (2001), pp. 1051-1056.
10. Sparrow J R, Fishkin N, Zhou J, Cai B, Jang Y P, Krane S, Itagaki Y, Nakanishi K. A2E, a byproduct of the visual cycle. Vision Res. 2003 December; 43(28):2983-90
11. Radu R A, Han Y, Bui T V, Nusinowitz S, Bok D, Lichter J, Widder K, Travis G H, Mata N L. Reductions in serum vitamin A arrest accumulation of toxic retinal fluorophores: a potential therapy for treatment of lipofuscin-based retinal diseases. Invest Ophthalmol Vis Sci. 2005 December; 46(12):4393-401
12. Motani A, Wang Z, Conn M, Siegler K, Zhang Y, Liu Q, Johnstone S, Xu H, Thibault S, Wang Y, Fan P, Connors R, Le H, Xu G, Walker N, Shan B, Coward P. Identification and characterization of a non-retinoid ligand for retinol-binding protein 4 which lowers serum retinol-binding protein 4 levels in vivo. J Biol. Chem. 2009 Mar. 20; 284(12): 7673-80.
13. Berni R, Formelli F. In vitro interaction of fenretinide with plasma retinol-binding protein and its functional consequences. FEBS Lett. 1992 Aug. 10; 308(1):43-5.
14. Schaffer E M, Ritter S J, Smith J E. N-(4-hydroxyphenyl) retinamide (fenretinide) induces retinol-binding protein secretion from liver and accumulation in the kidneys in rats. J. Nutr. 1993 September; 123(9):1497-503
15. Adams W R, Smith J E, Green M H. Effects of N-(4-hydroxyphenyl)retinamide on vitamin A metabolism in rats. Proc Soc Exp Biol Med. 1995 February; 208(2):178-85.
16. Puduvalli V K, Saito Y, Xu R, Kouraklis G P, Levin V A, Kyritsis A P. Fenretinide activates caspases and induces apoptosis in gliomas. Clin Cancer Res. 1999 August; 5(8): 2230-5
17. Holmes W F, Soprano D R, Soprano K J. Synthetic retinoids as inducers of apoptosis in ovarian carcinoma cell lines. J Cell Physiol. 2004 June; 199(3):317-29
18. Simeone A M, Ekmekcioglu S, Broemeling L D, Grimm E A, Tari A M. A novel mechanism by which N-(4-hydroxyphenyl)retinamide inhibits breast cancer cell growth: the production of nitric oxide. Mol Cancer Ther. 2002 October; 1(12):1009-17
19. Fontana J A, Rishi A K. Classical and novel retinoids: their targets in cancer therapy. Leukemia. 2002 April; 16(4):463-72
20. Samuel W, Kutty R K, Nagineni S, Vijayasarathy C, Chandraratna R A, Wiggert B. N-(4-hydroxyphenyl)retinamide induces apoptosis in human retinal pigment epithelial cells: retinoic acid receptors regulate apoptosis, reactive oxygen species generation, and the expression of heme oxygenase-1 and Gadd153. J Cell Physiol. 2006 December; 209(3):854-65
21. Fontana J A, Rishi A K. Classical and novel retinoids: their targets in cancer therapy. Leukemia. 2002 April; 16(4):463-72
22. Samuel W, Kutty R K, Nagineni S, Vijayasarathy C, Chandraratna R A, Wiggert B. N-(4-hydroxyphenyl)retinamide induces apoptosis in human retinal pigment epithelial cells: retinoic acid receptors regulate apoptosis, reactive oxygen species generation, and the expression of heme oxygenase-1 and Gadd153. J Cell Physiol. 2006 December; 209(3):854-65
23. Sabichi A L, Xu H, Fischer S, Zou C, Yang X, Steele V E, Kelloff G J, Lotan R, Clifford J L. Retinoid receptor-dependent and independent biological activities of novel fenretinide analogues and metabolites. Clin Cancer Res. 2003 Oct. 1; 9(12):4606-13
24. Clifford J L, Menter D G, Wang M, Lotan R, Lippman S M. Retinoid receptor-dependent and -independent effects of N-(4-hydroxyphenyl)retinamide in F9 embryonal carcinoma cells. Cancer Res. 1999 Jan. 1; 59(1):14-8.
25. Gollapalli D R, Rando R R. The specific binding of retinoic acid to RPE65 and approaches to the treatment of macular degeneration. Proc Natl Acad Sci USA. 2004 Jul. 6; 101(27):10030-5

26. Maiti P, Kong J, Kim S R, Sparrow J R, Allikmets R, Rando R R. Small molecule RPE65 antagonists limit the visual cycle and prevent lipofuscin formation. Biochemistry. 2006 Jan. 24; 45(3):852-60
27. Radu R A, Mata N L, Nusinowitz S, Liu X, Sieving P A, Travis G H. Treatment with isotretinoin inhibits lipofuscin accumulation in a mouse model of recessive Stargardt's macular degeneration. Proc Natl Acad Sci USA. 2003 Apr. 15; 100(8):4742-7
28. Monaco H L, Rizzi M, Coda A. Structure of a complex of two plasma proteins: transthyretin and retinol-binding protein. Science. 1995 May 19; 268(5213):1039-41.
29. Bonanni B, Lazzeroni M, Veronesi U. Synthetic retinoid fenretinide in breast cancer chemoprevention. Expert Rev Anticancer Ther. 2007 April; 7(4):423-32.
30. Sunness J S, Margalit E, Srikumaran D, Applegate C A, Tian Y, Perry D, Hawkins B S, Bressler N M. The long-term natural history of geographic atrophy from age-related macular degeneration: enlargement of atrophy and implications for interventional clinical trials. Ophthalmology. 2007 February; 114(2):271-7.
31. Glickman J F et al. A comparison of ALPHAScreen, TR-FRET, and TRF as assay methods for FXR nuclear receptors. J. Biomol. Screening 2002; 7:3-10
32. Fujimura T et al. Unique properties of coactivator recruitment caused by differential binding of FK614, an antidiabetic agent, to PPARgamma. Biol. Pharm. Bull. 2006; 29:423-429
33. Zhou G et al. Nuclear receptors have distinct affinities for coactivators: characterization by FRET. Mol. Endocrinol. 1998; 12:1594-1605
34. Cogan U, Kopelman M, Mokady S, Shinitzky M. Binding affinities of retinol and related compounds to retinol binding proteins. Eur J. Biochem. 1976 May 17; 65(1):71-8.
35. Decensi A, Torrisi R, Polizzi A, Gesi R, Brezzo V, Rolando M, Rondanina G, Orengo M A, Formelli F, Costa A. Effect of the synthetic retinoid fenretinide on dark adaptation and the ocular surface. J Natl Cancer Inst. 1994 Jan. 19; 86(2):105-10.
36. Conley B, O'Shaughnessy J, Prindiville S, Lawrence J, Chow C, Jones E, Merino M J, Kaiser-Kupfer M I, Caruso R C, Podgor M, Goldspiel B, Venzon D, Danforth D, Wu S, Noone M, Goldstein J, Cowan K H, Zujewski J. Pilot trial of the safety, tolerability, and retinoid levels of N-(4-hydroxyphenyl) retinamide in combination with tamoxifen in patients at high risk for developing invasive breast cancer. J Clin Oncol. 2000 January; 18(2):275-83.
37. Fain G L, Lisman J E. Photoreceptor degeneration in vitamin A deprivation and retinitis pigmentosa: the equivalent light hypothesis. Exp Eye Res. 1993 September; 57(3): 335-40.
38. Makimura H, Wei J, Dolan-Looby S E, Ricchiuti V, Grinspoon S. Retinol-Binding Protein Levels are Increased in Association with Gonadotropin Levels in Healthy Women. Metabolism. 2009 April; 58(4): 479-487.
39. Yang Q, Graham T E, Mody N, Preitner F, Peroni O D, Zabolotny J M, Kotani K, Quadro L, Kahn B B. Serum retinol binding protein 4 contributes to insulin resistance in obesity and type 2 diabetes. Nature. 2005 Jul. 21; 436 (7049):356-62.
40. Kim S R, Jang Y P, Jockusch S, Fishkin N E, Turro N J, Sparrow J R. The all-trans-retinal dimer series of lipofuscin pigments in retinal pigment epithelial cells in a recessive Stargardt disease model. PNAS. Dec. 4, 2007, Vol. 104, No. 49, 19273-8.
41. Wu Y, Fishkin N E, Pande A, Pande J, Sparrow R J. Novel Lipofuscin Bisretinoids Prominent in Human Retina and in a Model of Recessive Stargardt Disease. Journal of Biological Chemistry. Jul. 24, 2009, Vol. 284, No. 30, 20155-20166.

What is claimed is:

1. A method for treating bisretinoid-mediated macular degeneration in a mammal afflicted therewith comprising administering to the mammal an effective amount of a compound having the structure:

or an ester or a pharmaceutically acceptable salt thereof.

2. The method of claim 1, wherein the amount is effective to lower the serum concentration of RBP4 in the mammal.

3. The method of claim 1, wherein the amount is effective to lower the retinal concentration of a bisretinoid in lipofuscin in the mammal.

4. The method of claim 3, wherein the bisretinoid is A2E, isoA2E, A2-DHP-PE, or atRAL di-PE.

5. The method of claim 1, wherein the bisretinoid-mediated macular degeneration is Age-Related macular Degeneration.

6. The method of claim 1, wherein the bisretinoid-mediated macular degeneration is Stargardt Disease.

7. The method of claim 1, wherein the bisretinoid-mediated macular degeneration comprises the accumulation of lipofuscin deposits in the retinal pigment epithelium.

8. The method of claim 2, wherein the amount is effective to lower the retinal concentration of a bisretinoid in lipofuscin in the mammal.

9. The method of claim 4, wherein the bisretinoid is A2E.

10. The method of claim 4, wherein the bisretinoid is isoA2E.

11. The method of claim 4, wherein the bisretinoid is A2-DHP-PE.

12. The method of claim 4, wherein the bisretinoid is atRAL di-PE.

13. The method of claim 4, wherein the bisretinoid-mediated macular degeneration is Age-Related Macular Degeneration.

14. The method of claim 4, wherein the bisretinoid-mediated macular degeneration is Stargardt Disease.

* * * * *